(12) United States Patent
Alon

(10) Patent No.: US 11,000,326 B1
(45) Date of Patent: May 11, 2021

(54) ORTHOPEDIC FASTENER AND ASSOCIATED SYSTEMS AND METHODS

(71) Applicant: Guy Alon, Davie, FL (US)

(72) Inventor: Guy Alon, Davie, FL (US)

( * ) Notice: Subject to any disclaimer, the term of this patent is extended or adjusted under 35 U.S.C. 154(b) by 159 days.

(21) Appl. No.: 16/434,132

(22) Filed: Jun. 6, 2019

Related U.S. Application Data

(60) Provisional application No. 62/682,430, filed on Jun. 8, 2018.

(51) Int. Cl.
*A61B 17/86* (2006.01)
*A61B 17/70* (2006.01)

(52) U.S. Cl.
CPC ........ *A61B 17/863* (2013.01); *A61B 17/7001* (2013.01); *A61B 17/8605* (2013.01); *A61B 17/8635* (2013.01); *A61B 17/866* (2013.01); *A61B 2017/8655* (2013.01)

(58) Field of Classification Search
CPC ..... A61B 17/7001; A61B 17/84; A61B 17/86; A61B 17/8625; A61B 17/863; A61B 17/8635; A61B 2017/8655; A61B 17/866; F16B 25/0057; F16B 25/0068; F16B 25/0089
See application file for complete search history.

(56) References Cited

U.S. PATENT DOCUMENTS 7,101,133 B2 * 9/2006 Dicke ................ F16B 25/0047
411/387.4

* cited by examiner

*Primary Examiner* — Larry E Waggle, Jr.
(74) *Attorney, Agent, or Firm* — Moyles IP, LLC

(57) ABSTRACT

An orthopedic fastener having compound parabolic petals configured to secure within trabecular bone during orthopedic procedures by compressing the trabecular bone while minimizing the lacerating effect of traditional screws and correspondingly reducing trauma to the trabecular bone. The compound parabolic petals are configured to progressively compress the trabecular bone during advancement of the orthopedic fastener through the trabecular bone in a compress-partial release-compress progression along a shaft of the orthopedic fastener and create a secure connection thereto with compression distributed along the length of the orthopedic fastener, and center a proximal end of the shaft/orthopedic fastener within an insertion point of the orthopedic fastener.

20 Claims, 10 Drawing Sheets

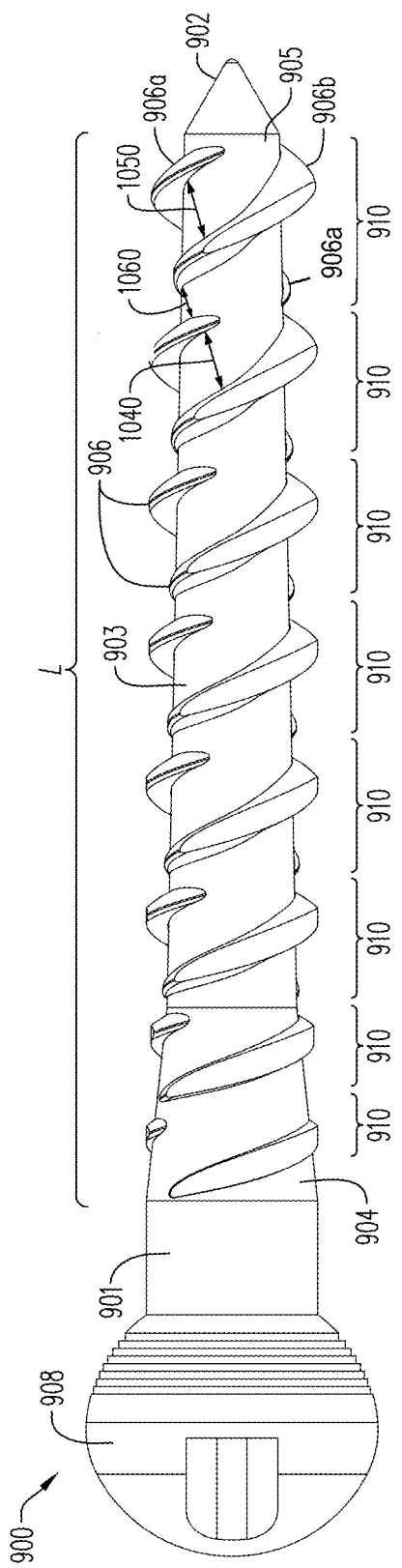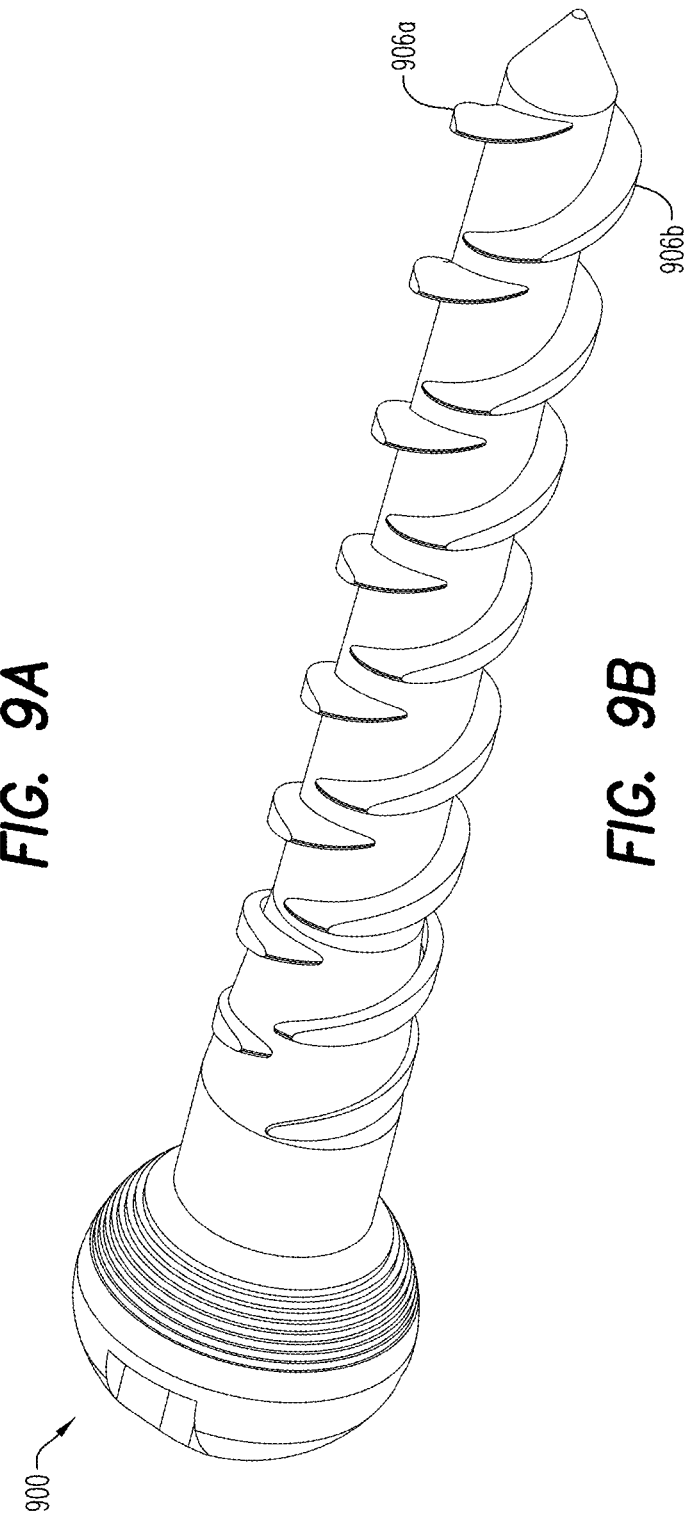

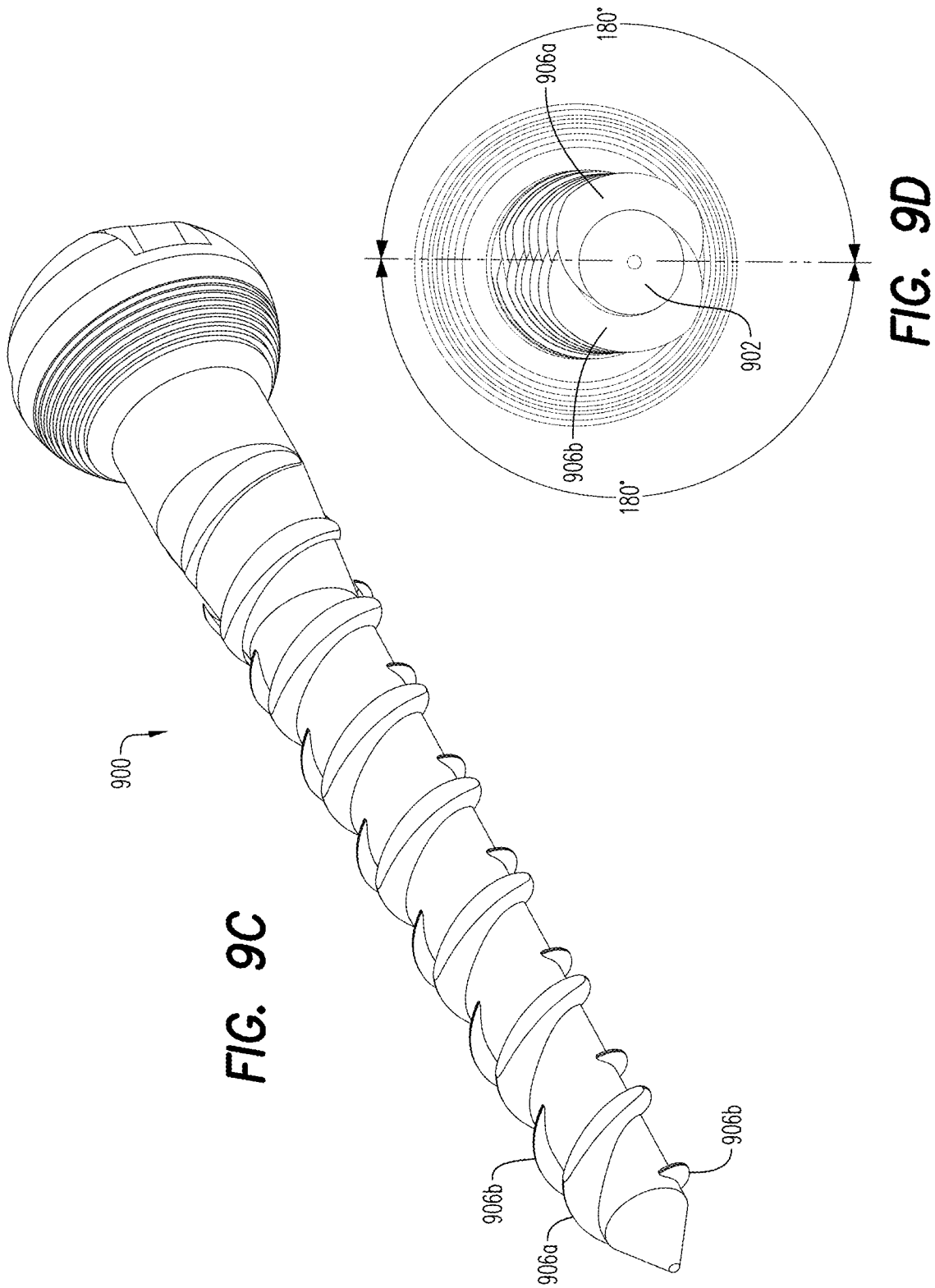

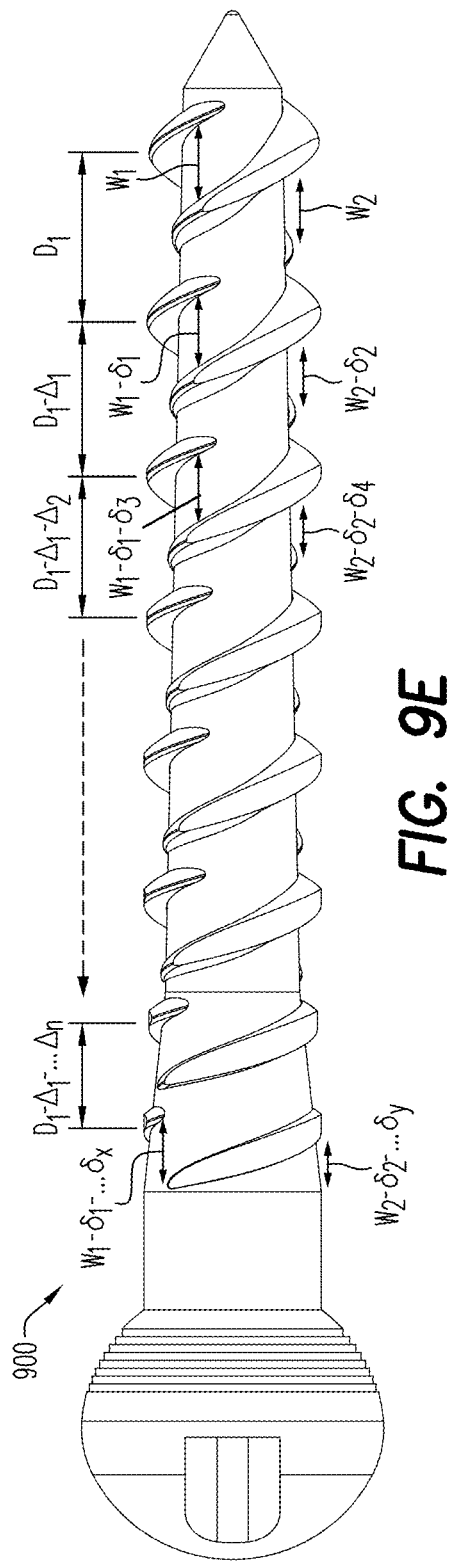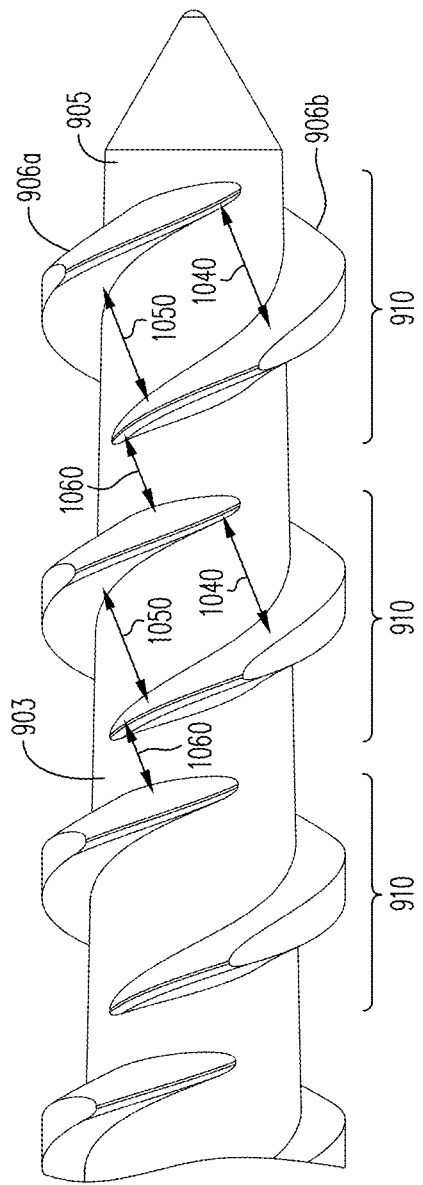
FIG. 9E
FIG. 10

ORTHOPEDIC FASTENER AND ASSOCIATED SYSTEMS AND METHODS

CROSS-REFERENCE TO RELATED APPLICATIONS

This application claims the benefit of U.S. Provisional Patent Application No. 62/682,430 filed Jun. 8, 2018, the entire contents of which are incorporated herein by reference.

BACKGROUND OF THE DISCLOSURE

It is common for trauma, oral and maxillofacial, bone reconstruction, total joint reconstruction or orthopedic corrective procedures for various deformity (collectively, "orthopedic procedures") to utilize surgical intervention to reconstruct, repair injured or failing joints or bones. Often during orthopedic procedures, securing or fastening bones, teeth, tissues, or other devices to bones is necessary. The devices, systems, and methods used to perform these fixations are critical for minimizing patient trauma, disability and recovery time, and ensuring that the fixation remains secured. In one regard, the devices and methods for these procedures must interact with the specific structure of bone. For example, fasteners must pierce surrounding tissue and the bone and secure therein. Less movement of the fracture ends, fragments, or fixation device typically correlates to shorter healing time, increased stability and more functional utility of the repair, although complete rigidity is not necessarily desirable.

In one aspect, trabecular bone is a focal point for bone damage during orthopedic procedures. With reference to FIG. 1, trabecular bone 102, also referred to as cancellous bone, is a generally spongy, porous type of bone that is found at the ends of long bones and within flat and irregular bones such as the sternum, pelvis, and spine. Trabecular bone 102 may be contained within denser cortical bone surfaces 101.

FIG. 2 shows finite structures of trabecular bone 102 (with continuing reference to FIG. 1). At the micro- 201 and nano- 202 structure scales the lattice-type configuration of trabecular bone 102 may be seen. The lattice includes bridges 203 of trabecular bone material (described in further detail, below) with interstices therebetween. Trauma or lacerations to the bone material bridges 203 can weaken entire portions of the lattice. The nano-structure scale 202 shows that successive bridges 203 of bone material may be supported by and/or connected to other discrete formations within the trabecular bone 102. Thus, damage to one portion of the lattice may affect the integrity of other portions.

Each trabecular bone cell also includes nucleotides which provide a communication channel between trabecular bone cells within a larger bone structure. Accordingly, minimizing the scar tissue in the insertion area and leveraging the nucleotide connections between all bone cells in a given bone structure is important since it allows for the bone to leverage the natural characteristics of bone and encourage adjacent cells to come to the aid of any impacted cells and provide additional anchoring stability in the overall bone structure. This is especially important when surgical fasteners and other orthopedic fixation devices are used on the bone to correct deformity and require maximum stability for thorough healing.

All of the above aspects of trabecular bone are susceptible to damage during orthopedic procedures of all kinds. For example, to fix an orthopedic device to a bone a surgeon may drill an insertion point through one of the cortical bone surfaces, advance a fastener through the insertion point and trabecular bone to secure the orthopedic device, and anchor the fastener in the cortical wall distal to the insertion point. A fastener that must pierce and secure itself within the trabecular bone can potentially traumatize or lacerate the trabecular bone and/or damage the nucleotide connections between trabecular bone cells.

Damage to the trabecular bone can increase healing time and scar tissue. This, in turn, reduces the effectiveness of the repair as the bone attempts to adjust to any fasteners, fixtures, or manipulations from the orthopedic procedure. Further, trabecular bone injury weakens the entire bone and hinders the natural biological bone remodeling whereby the trabecular bone structure naturally changes over the course the bone's life and adjusts to or prevents further damage from repeated forces. Damage to the trabecular bone stimulates a rigid bone remodeling to compensate for the damage. The damaged portions of trabecular bone become incapable of natural bone remodeling. Thus, more damage to the natural structure of the trabecular bone leads to more bone with diminished ability to adjust to repeated forces and/or prevent further damage or injury.

Current screws, fasteners, and other devices used in orthopedic procedures can damage the trabecular bone. For example, the devices may manipulate and artificially fixate bone fragments including trabecular bone to fix the device(s) in place. The manipulation and fixation may traumatize the trabecular bone by, e.g., indiscriminately stressing, fracturing, and shifting portions of the bone. In addition, some screws and fasteners employ sharp threading that can lacerate the trabecular bone and surrounding tissues.

In addition, the devices and systems used in the subject procedures often fracture, loosen, or even disengage from fixations. Any of these can cause further damage to the bone and may require additional orthopedic procedures to remedy.

The current devices, systems, and associated methods also have some difficulty interfacing with many patient co-morbidities: osteopenia and osteoporosis, Parkinson's Disease, diabetes mellitus, among others.

In view of the above, there is a need for an orthopedic fastener that minimizes trauma and injury to tissues and bone, especially trabecular bone, during orthopedic procedures and prevents fracturing, loosening, or disengaging of the orthopedic fastener over the life of the implant once it is in place.

BRIEF DESCRIPTION OF THE EXEMPLARY EMBODIMENTS

For purposes of this disclosure, "orthopedic fastener" generally and without limitation means a device or system for securing, fixing, or attaching bones, tissues, muscles, implanted devices, etc. to a bone or body structure.

In an aspect, the disclosure relates to an exemplary embodiment of an orthopedic fastener comprising a head portion; a tip portion; a shaft having a proximal end connected to the head portion and a distal end connected to the tip portion; and, a plurality of compound parabolic petals extending helically around the shaft and defining gaps between circumferentially overlapping portions of petals, wherein the petals are configured to compress trabecular bone in the gaps and in a direction perpendicular to the insertion direction of the orthopedic fastener in a bone.

In another aspect, the disclosure relates to an orthopedic fastening system, comprising: an orthopedic fastener having: a head portion; a connecting bulb connected to the head portion; a tip portion; a shaft having a proximal end connected to the head portion and a distal end connected to the tip portion; and a plurality of compound parabolic petals extending helically around the shaft and defining gaps between circumferentially overlapping portions of petals, wherein the petals are configured to compress trabecular bone in the gaps and in a direction perpendicular to the insertion direction of the orthopedic fastener in a bone; an annular, polyaxial articulating head having first and second apertures along a diameter of the polyaxial articulating head; and, a torsion rod, wherein the polyaxial articulating head is configured to receive the connecting bulb, move polaxially about the connecting bulb, and receive the torsion rod through the first and second apertures, and, the polyaxial articulating head is further configured to rotate and thereby advance the orthopedic fastener through a bone when the torsion rod is turned and maintain the path of the orthopedic fastener through the bone regardless of the polyaxial orientation of the articulating head.

In a further aspect, the disclosure relates to a compound parabolic petal for an orthopedic fastener, comprising: a proximal face; a distal face; and, a capped crest, wherein the proximal face has a transition between an undercut and an overcut parabolic portion and the undercut parabolic portion is configured to compress trabecular bone, the distal face has at least one overcut parabolic portion, and the capped crest has compound curved leading and trailing edges.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which:

FIG. 9A shows a side perspective view of an exemplary 2-petal embodiment of an orthopedic fastener according to the disclosure;

FIG. 9B shows a top perspective view of an exemplary 2-petal embodiment of an orthopedic fastener according to the disclosure;

FIG. 9C shown an opposite top perspective view of an exemplary 2-petal embodiment of an orthopedic fastener according to the disclosure;

FIG. 9D shows a front plan view of an exemplary 2-petal embodiment of an orthopedic fastener according to the disclosure;

FIG. 9E shows a side perspective view of an exemplary 2-petal embodiment of the orthopedic fastener with general dimensions;

FIG. 10 shows an enlarged view of exemplary compound parabolic petals in an exemplary 2-petal embodiment of the orthopedic fastener according to the disclosure; and, FIG. 11 shows an exemplary surgical system for use with the exemplary orthopedic fastener according to the disclosure.

Figure 1:
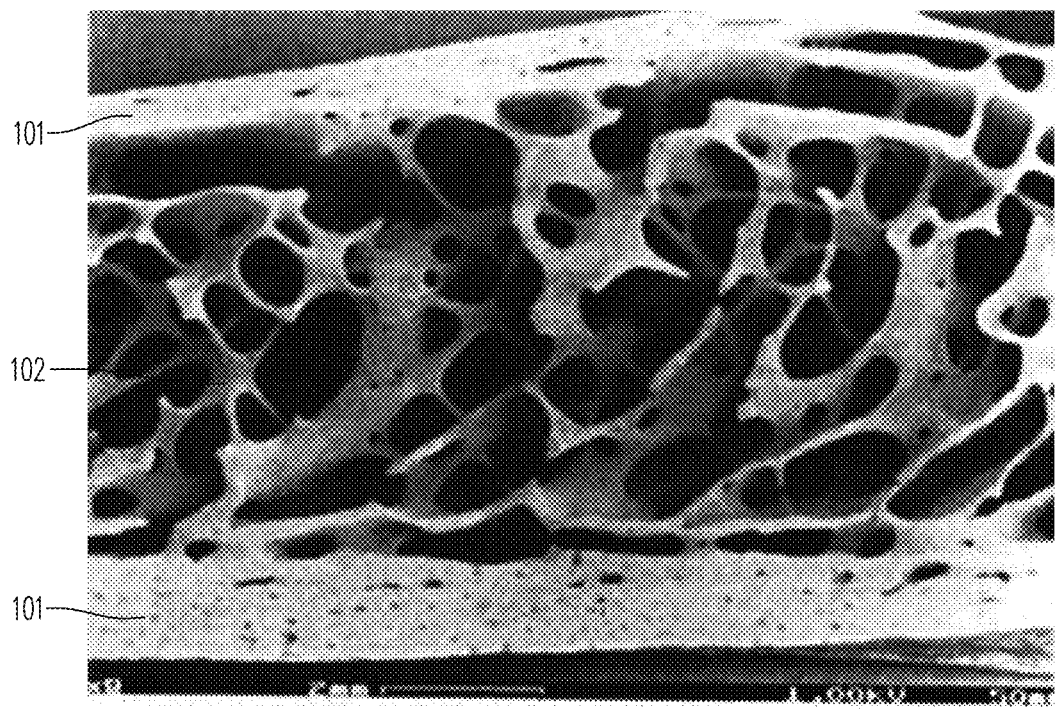
FIG. 1 shows a micrograph of trabecular bone.

Various features, aspects, and advantages of the embodiments will become more apparent from the following detailed description, along with the accompanying figures in which like numerals represent like components throughout the figures and text. The various described features are not necessarily drawn to scale but may be drawn to emphasize specific exemplary features.

The headings used herein are for organizational purposes only and are not meant to limit the scope of the description of the claims. To facilitate understanding, reference numerals have been used, where possible, to designate like elements common to the figures.

DETAILED DESCRIPTION OF THE EXEMPLARY EMBODIMENTS

Reference will now be made in detail to exemplary embodiments of the disclosed devices, systems, and methods. Each example is provided by way of explanation and is not meant as a limitation and does not constitute a definition of all possible embodiments.

Figure 2:
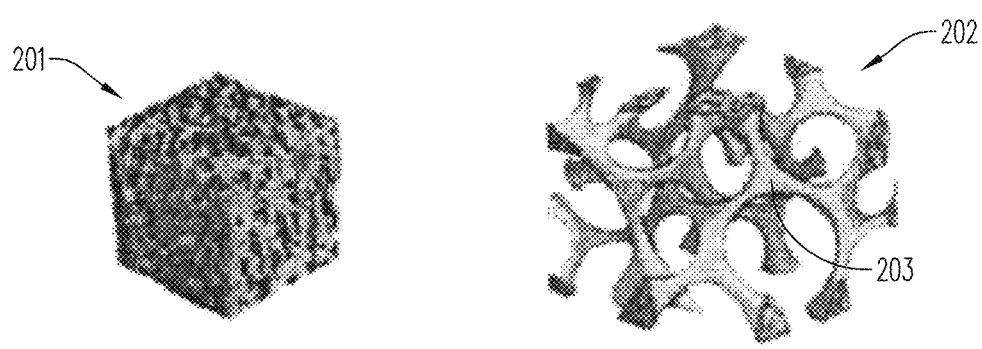
FIG. 2 shows scaled depictions of trabecular bone.
Figure 3A:
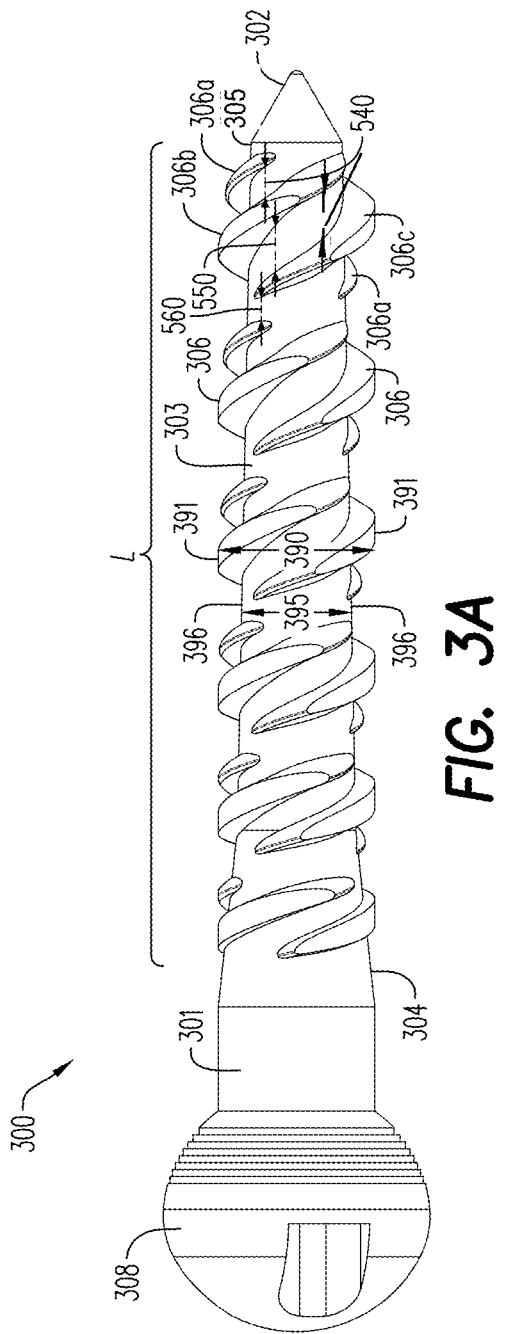
FIG. 3A shows a side perspective view of an exemplary 3-petal orthopedic fastener according to the disclosure.

An exemplary orthopedic fastener 300 according to the disclosure is shown in FIG. 3A. The exemplary orthopedic fastener 300 reduces trauma to trabecular bone by, among other things, passing or plowing through interstices between bone material bridges 203 (FIG. 2) instead of piercing, fracturing, or lacerating the trabecular bone, and securing itself in the trabecular bone by compressing the bone material bridges 203 together and in a direction that is both axial along the length of the shaft and perpendicular to the shaft and insertion direction of the orthopedic fastener 300 as described below.

The exemplary orthopedic fastener 300 shown in FIG. 3A includes, among other things, a head portion 301, a tip 302, and a shaft 303 having a proximal end 304 connected to the head portion 301 and a distal end 305 connected to the tip 302 and extending there between. A plurality of petals 306 including petals 306a, 306b, and 306c, discussed further below, are arranged helically around the shaft 303 such that portions of different petals 306 circumferentially overlap along a length L of the shaft 303 and form gaps 540, 550, 560 (explained in detail further below with respect to FIG. 5) between circumferentially overlapping portions of petals 306. The exemplary orthopedic fastener 300 further includes a major diameter 390 and a minor diameter 395. For purposes of this disclosure, the major diameter 390 is the largest diameter at a given point between two lines representing the outline of the orthopedic fastener 300, for example the diameter between the respective crests 391 of two petals 306 located on opposite sides of the shaft 303. This could be, for example and without limitation, a parallel outline, a tapered or conical outline, or a form of a curve similar to the outline of a bullet. In an aspect, an exemplary major diameter range for the exemplary embodiments herein is from approximately 1.8 mm for a small orthopedic fastener used in, e.g., a distal radius of a bone, to 40 mm for a hip, knee, or ankle total joint orthopedic fastener. In an aspect, the major diameter 390 may be tapered to accommodate the specific needs of the application. For example, in a total knee joint orthopedic fastener, the major diameter may have a taper between approximately 0 degrees and 20 degrees The minor diameter 395 is the distance between the respective roots 396 of two petals 306 located on opposite sides of the shaft 303. An exemplary minor diameter 395 range for the shaft 303 in this application is from approximately 1.2 mm for a small orthopedic fastener used in, e.g., a distal radius of a bone, to 25 mm for a hip, knee, or ankle total joint orthopedic fastener.

Figure 5:
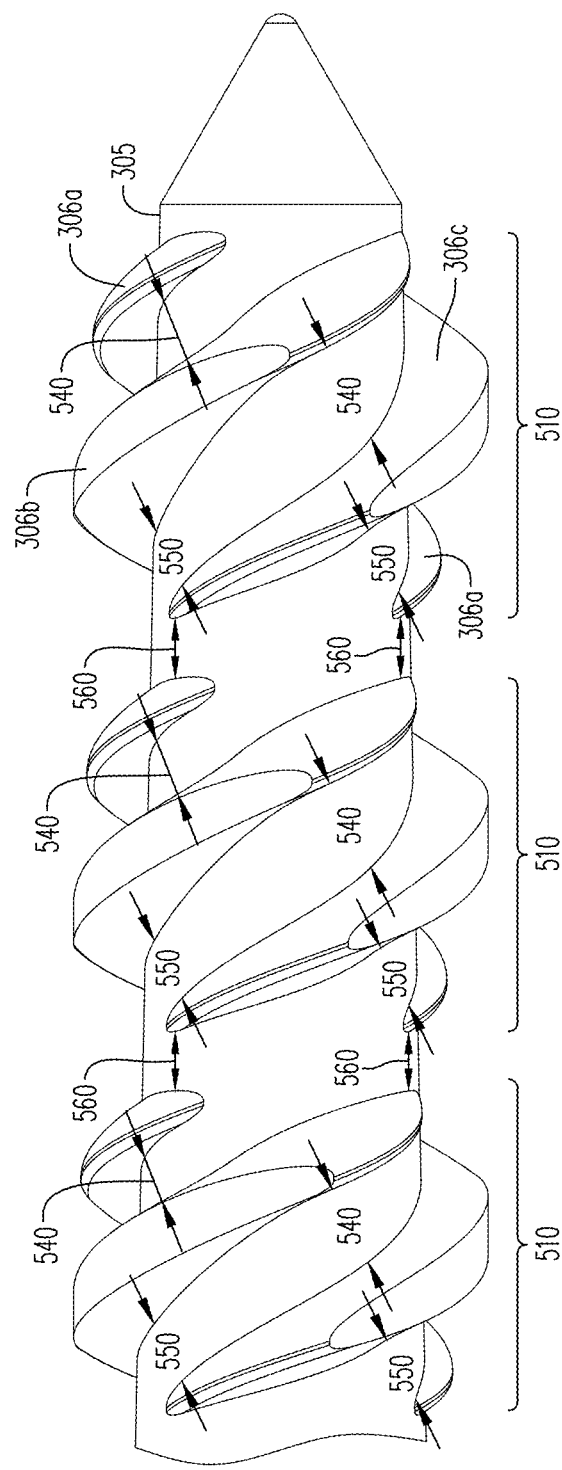
FIG. 5 shows an enlarged view of a portion of an exemplary 3-petal orthopedic fastener according to the disclosure.
Figure 6:
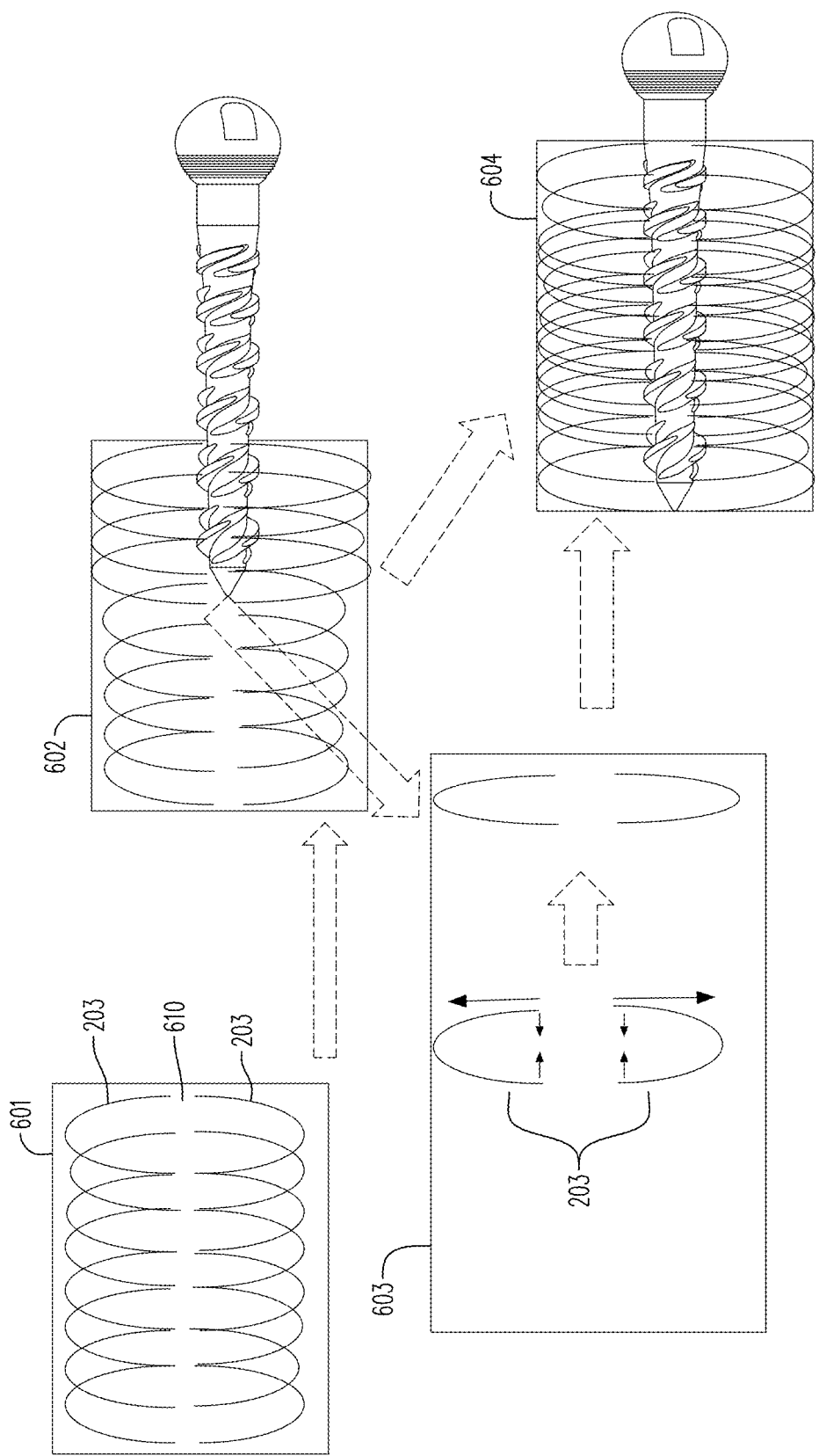
FIG. 6 shows compression of trabecular bone by an exemplary orthopedic fastener according to the disclosure.

The helical configuration of the petals 306 compresses trabecular bone in gaps 540 (FIG. 5) and in a direction perpendicular to the insertion direction of the orthopedic fastener 300 as described with respect to FIG. 6. The petals 306 have a compound parabolic configuration as described further below with respect to, for example, FIG. 7. Thus, for purposes of this disclosure, the phrases "petal(s)" or "blades" and "compound parabolic petal(s)" are interchangeable and refer to the exemplary disclosed embodiments of a compound parabolic petal.

Figure 3B:
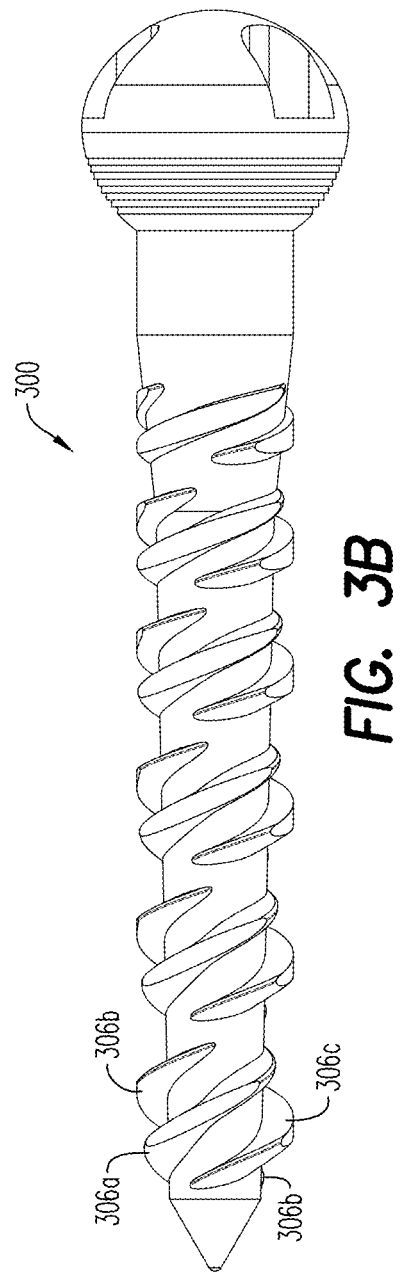
FIG. 3B shows an opposite side perspective of an exemplary 3-petal orthopedic fastener according to the disclosure.
Figure 3C:
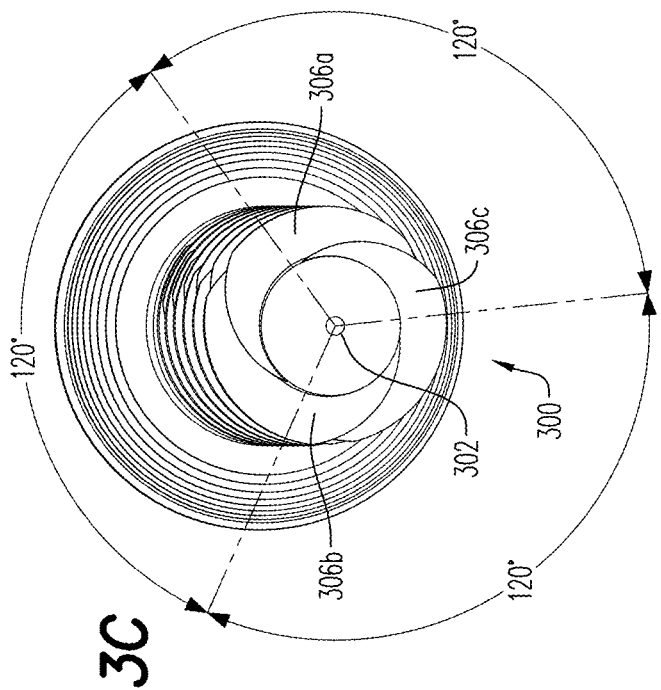
FIG. 3C shows a front plan view of an exemplary 3-petal orthopedic fastener according to the disclosure.

The exemplary helical configuration of the petals 306 and representative petals 306a, 306b, and 306c shown in FIG. 3A is further illustrated in the different perspective views of FIGS. 3B and 3C. FIGS. 3A-3C in conjunction show the exemplary helical configuration around the circumference of the shaft 303. As shown in FIG. 3A and with reference in a direction from the distal end 305 towards the proximal end 304 of the shaft 303, petal 306a begins in the view of FIG. 3A, wraps out of view behind the shaft 303, and continues to wrap around the shaft 303 and ends back in the view of FIG. 3A. Petal 306b begins and ends behind the shaft out of the view of FIG. 3A which shows an intermediate portion of the petal 306b wrapping around the shaft 303 from its beginning to its end. Petal 306c begins behind the shaft out of view of FIG. 3A, wraps around the shaft 303, and ends in the view of FIG. 3A.

FIG. 3B shows a view behind the shaft 303 from the view of FIG. 3A and the corresponding helical configuration of the petals 306, including petals 306a, 306b, and 306c, that is out of the view of FIG. 3A. For example, FIG. 3B shows an intermediate portion of petal 306a wrapping around the shaft 303 from its beginning to its end which are shown in FIG. 3A. Further, the beginning and end of petal 306b, not visible in FIG. 3A, are shown in FIG. 3B. Petal 306b begins in the view of FIG. 3b, wraps out of view to the intermediate portion shown in FIG. 3A, and continues to wrap around the shaft 303 and ends back in the view of FIG. 3B. In addition, FIG. 3B shows the beginning of petal 306c which wraps around the shaft 303 to its end shown in FIG. 3A.

FIGS. 3A and 3B illustrate the overlapping configuration of the petals 306 in an exemplary embodiment. With continuing reference to the view shown in FIG. 3A and in a direction from the distal end 305 to the proximal end 304 of the shaft 303, petal 306a begins closest (as between petals 306a, 306b, and 306c) to the distal end 305, overlaps petals 306b and 306c, and ends farthest from the distal end 305. On the other hand, in the view of FIG. 3B petal 306b begins closest to the distal end 305, overlaps petals 306c and 306a, and ends farthest from the distal end 305 in the view of FIG. 3B. This overlapping helical configuration of the petals 306 contributes to the exemplary disclosed compression of trabecular bone. As discussed further below with respect to FIG. 5, the arrangement of representative petals 306a-306c constitutes a repeating set (e.g., 510) of three petals that is repeated along the length L of the shaft 303 in the exemplary embodiment.

FIG. 3C shows the exemplary orthopedic fastener 300 shown in FIGS. 3A and 3B from the perspective along the tip 302. As shown in FIG. 3C, the exemplary helical configuration of petals 306, by reference to representative petals 306a, 306b, and 306c, is also achieved in part by spacing the beginning and ends of successive petals 306a, 306b, 306c at 120 degrees apart around the circumference of the shaft 303. In other embodiments the petals 306 may be spaced at whatever interval is required for a particular application consistent with this disclosure.

Figure 4:
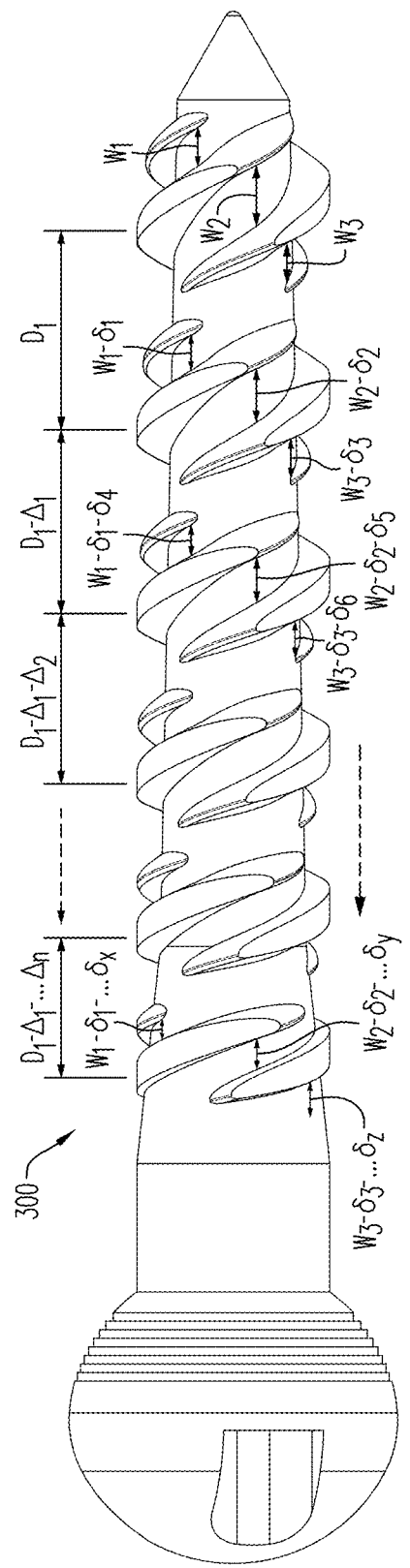
FIG. 4 shows a side perspective view of an exemplary 3-petal orthopedic fastener with general dimensions according to the disclosure.

Other dimensional aspects of the exemplary disclosed embodiment of an orthopedic fastener 300 shown in FIGS. 3A-3C are shown in FIG. 4. As shown in FIG. 4, and with continuing reference to FIG. 3A, the exemplary embodiment includes at least one distance, e.g., $D_1$, between successive petals 306 along the same circumferential angle on the shaft 303 and widths $W_1$-$W_3$ between petals 306. In one aspect of the exemplary embodiment shown in FIG. 4, the distance between petals 306 progressively decreases in a direction from the distal end 305 to the proximal end 304. Accordingly, the distance between successive petals 306 along the same circumferential angle on the shaft 303 will progressively decrease from $D_1$, to $D_1$-$\Delta_1$, to $D_1$-$\Delta_1$-$\Delta_2$, and through to $D_1$-$\Delta_1$-...$\Delta_n$, where $\Delta_1$, $\Delta_2$, ... and $\Delta_n$ can be any suitable value depending on the particular application and requirements for the orthopedic fastener 300. Similarly, the widths $W_1$-$W_3$ between petals 306 will decrease respectively from $W_1$, $W_2$, and $W_3$, to $W_1$-$\delta_1$, $W_2$-$\delta_2$, and $W_3$-$\delta_3$, to $W_1$-$\delta_1$-$\delta_4$, $W_2$-$\delta_2$-$\delta_5$, and $W_3$-$\delta_3$-$\delta_6$, through to $W_1$-$\delta_1$-$\delta_x$, $W_2$-$\delta_2$-$\delta_y$, and $W_3$-$\delta_3$-$\delta_z$, where $\delta_1$, $\delta_2$, ... $\delta_z$ can be any suitable value depending on the particular application and requirements for the orthopedic fastener 300.

In the exemplary disclosed embodiments, the range of distances ($D_1$, etc.) between successive petals 306 along the same circumferential angle of the shaft 303, including on the same orthopedic fastener 300 with progressive dimensions as discussed above, may be from approximately 1.5 mm to about 15 mm. The range of widths ($W_1$, etc.) between directly adjacent petals 306 may be from approximately 0.5 mm to about 7.5 mm, and the range of petal heights h (see FIG. 7) may be from approximately 0.1 mm to about 12.5 mm. The exemplary dimensions are not meant to limit the scope of the disclosure and the range(s) of dimensions may accommodate for, among other things, the needs in the design of a total joint orthopedic fastener. The actual dimensions may vary widely depending upon factors including but not limited to the density, rigidity, and liquid content of the trabecular bone at the fixation site, the degree of trabecular bone compression sought between successive petals, and the ratio of the major diameter 390 to the minor diameter 395 of a particular orthopedic fastener for fixation in a particular bone (because of additional radial compression not just from the standpoint of axial compression along the length of the cells, but the compression of the trabecular bone from the conical cross-section of the minor diameter 395 against the cortical walls (see FIG. 6)—i.e., the conical cross-section of the minor diameter 395 allows compression of the trabecular bone against the cortical walls wherein a bigger (diameter) shaft squeezes the trabecular bone further toward the cortical walls). Other factors for dimensioning the exemplary orthopedic fastener (e.g., 300) that affect the above considerations and others involve, for example and without limitation, the bone or region (i.e., spinal, facial, total joint, etc.) for fixation, the age/development of the patient, the forces that are likely to act on the fastener, etc.

Other dimensions that will vary depending on the size of the bone, application, patient, injury, forces acting on the orthopedic fastener, etc. are the circumferential length of the petals 306 extending around the shaft, the length L of the shaft, and the minor diameter 395, as explained further below with respect to certain exemplary embodiments.

By way of example, in areas such as the thoracic-lumbar region, trabecular bone is relatively denser and harder given that it has to support more weight from the rest of the spine, head, neck, and other forces above it. Here, the fastener must anchor itself into the medium of the insertion point with maximum strength while taking into consideration the limiting factors such as dimensional spaces available to the anchoring devices. For example, the insertion point is typically through the pedicle canal, which, due to its size, limits the available diameter for orthopedic fasteners. This limiting factor requires an anchoring device that resists axial (pull-out) as well as radial and in some cases torsional (within the medium) forces. In an aspect, changes in bone density may require a modification to the dimensions and spacing of the petals. Understanding the environment, the appropriate orthopedic fastener is capable both of withstanding the relevant forces over the lifetime of the patient while maximizing anchoring stability in either omni-directional or bi-directional configurations at a surgeon's discretion depending upon, e.g., the patient, the patient's age, the nature of the injury, bone health etc.

Another objective of the orthopedic fastener is to minimize trauma to the trabecular bone and reduce healing time. Accordingly, an orthopedic fastener may have, for example, a 3-petal design (as previously discussed for omni-directional stability) with relatively shorter distances between petals to fit dense, hard, trabecular bone. For example, in the exemplary disclosed orthopedic fastener 300, application(s) for lumbar fixation may include a range of distances between successive petals 306 along the same circumferential angle of the shaft 303 from approximately 4 mm to about 2.5 mm and a width between successive, adjacent petals 306 of approximately 1 mm. The height h range of the petals in this exemplary orthopedic fastener may be from approximately 0.2 mm to about 1.0 mm. The exemplary circumferential lengths of petals 306 extending around the shaft may be from a range of approximately 5 mm to 6.5 mm, and the length L range of the shaft may be approximately 6 mm to 150 mm. In the exemplary disclosed embodiment shown in FIGS. 3A-3C, the shaft is approximately 30 mm long. A more particular minor diameter range for the exemplary examples herein is from approximately 2.6 mm to 4 mm.

As further detailed with respect to FIG. 6, the orthopedic fastener 300 compresses the trabecular bone bridges (203) towards each other and in a direction perpendicular to the insertion direction of the orthopedic fastener 300. The trabecular bone cell size and density in the cervical and lumbar spine (discussed further below with respect to FIGS. 9A-10) are particularly well suited to the compression dynamics created by the disclosed orthopedic fastener 300 (900, FIG. 9A) for securing the orthopedic fastener 300 and avoiding trauma to the trabecular bone. Further, the insertion point for an orthopedic fastener in cervical and lumbar spinal fixation procedures is already perpendicular to the forces acting on the bone and the orthopedic fastener interacts with the natural trabecular bone structure substantially according to the exemplary compression dynamics described herein. For example, an orthopedic fastener in cervical and lumbar fixation procedures may pass along the base of the trabecular bone materials bridges 203 as opposed to penetrating through the bridges 203. For at least the above reasons, the exemplary disclosed orthopedic fastener 300 achieves a substantial degree of compression in both radial and axial directions of the cervical and lumbar spine and securement therein.

Progressively decreasing the distance between petals 306 progressively increases the amount of trabecular bone compression that the orthopedic fastener 300 generates as it advances through the trabecular bone and helps to distribute the compressive forces along the length L of the orthopedic fastener 300/shaft 303. For example, the leading tip 302 and distal end 305 of the orthopedic fastener 300 encounter and compress more trabecular bone than the proximal end 304 as the orthopedic fastener 300 travels through the trabecular bone. Decreasing the distance between petals 306 from the distal end 305 to the proximal end 304 compensates for the difference between the amount of trabecular bone encountered and compressed between the distal end 305 and the proximal end 304 and distributes compressive forces along the length L of the orthopedic fastener 300/shaft 303. Distributing the compressive forces along the length L of the orthopedic fastener 300/shaft 303 enhances securement of the orthopedic fastener 300.

The exemplary embodiment shown in FIGS. 3A-4 also includes a shaft 303 that tapers in a direction from the proximal end 304 to the distal end 305 to increase the amount of compression generated by the orthopedic fastener 300 and distribute compressive forces along the length L of the orthopedic fastener 300/shaft 303. As the exemplary orthopedic fastener 300 is advanced through trabecular bone, the increasing diameter of the shaft 303 coupled with the axial compressive characteristics of the design provides progressively increasing compression of the trabecular bone between the orthopedic fastener 300 and, e.g., the cortical walls. In the exemplary embodiment shown in FIGS. 3A-4, the shaft 303 is formed integrally with the head portion 301 and tip 302. In other embodiments, one or more of the shaft 303, head portion 301, and tip 302 may be separate components joined by welding, adhesive, or other known techniques.

The exemplary embodiment shown in FIGS. 3A-4 also includes a connecting bulb 308 connected to the head portion 301. The connecting bulb 308 connects to additional components of an orthopedic fastening system described further below with respect to FIG. 11. In other embodiments, the head portion 301 may take any form consistent with this disclosure. For example, head portion 301 may be attached to a variety of connectors for particular surgical systems or head portion 301 may be the connector for other components or surgical systems. Head portion 301 may also be integral with the shaft 303 and/or refer simply to the terminus of the shaft 303.

The tip 302 in the exemplary embodiment shown in FIGS. 3A-4 is cone-shaped. In other embodiments the tip 302 may be any shape capable of passing through trabecular bone. The orthopedic fastener 300 and/or particular features, such as tip 302, in the exemplary embodiment shown in FIGS. 3A-4 may be formed from any materials with sufficient strength, hardness, and other properties for the applications in which the orthopedic fastener 300 is used. Exemplary materials are those allowed by the FDA for permanent medical implants such as cobalt, chrome, and titanium and compounds thereof. The orthopedic fastener 300 including petals 306 and other features may be machined from a single piece of such material, molded by injection molding or other known techniques, assembled by joining different components by welding, adhesives, etc., or by any other process that meets particular objectives (such as practicality, cost, dimensional tolerances, etc.) and is consistent with the scope of this disclosure.

With reference now to FIG. 5, the configuration of petals 306 and gaps 540, 550, 560 in the exemplary orthopedic fastener 300 shown in FIGS. 3A-4 is illustrated in additional detail. As shown in FIG. 5, petals 306 in the exemplary embodiment are arranged in repeating sets 510 of three petals 306 (e.g., 306a, 306b, 306c). Repeating sets 510 are representatively shown in the blown-up view of the distal end 305 in FIG. 5 and it is understood that such repeating sets continue up the shaft 303 to the proximal end 304 as in the exemplary embodiment shown in FIGS. 3A-4.

The gaps 540, 550, 560 between petals 306 include compressive gaps 540, expansive gaps 550, and transition gaps 560. Compressive gaps 540 are created in part by undercut parabolic portions 701 of the petals 306 as described with respect to FIG. 7. The undercut and/or concave parabolic portions "scoop" and compress trabecular bone in the compressive gaps 540 as the orthopedic fastener 300 is turned and advanced through the trabecular bone in a similar fashion as a cupped hand scoops and compresses dirt while digging. For example, with reference to FIGS. 2 and 6, the orthopedic fastener 300 in use is, to the extent possible, passed along the base 610 of bridges of trabecular bone material 203. Before the orthopedic fastener 300 is inserted (shown in FIG. 6 as state 601), the bridges of trabecular bone material 203 are uncompressed. As the orthopedic fastener 300 is inserted (FIG. 6, state 602), the bridges of trabecular bone material 203 are compressed inwards and in a direction perpendicular to the insertion direction of the orthopedic fastener 300 (see arrows in detail 603) by compressive gaps 540. When the orthopedic fastener 300 is fully inserted (FIG. 6, state 604), the trabecular bone is compressed between the orthopedic fastener 300 and the cortical wall along the length of the orthopedic fastener 300, thus securing the orthopedic fastener 300.

Figure 7:
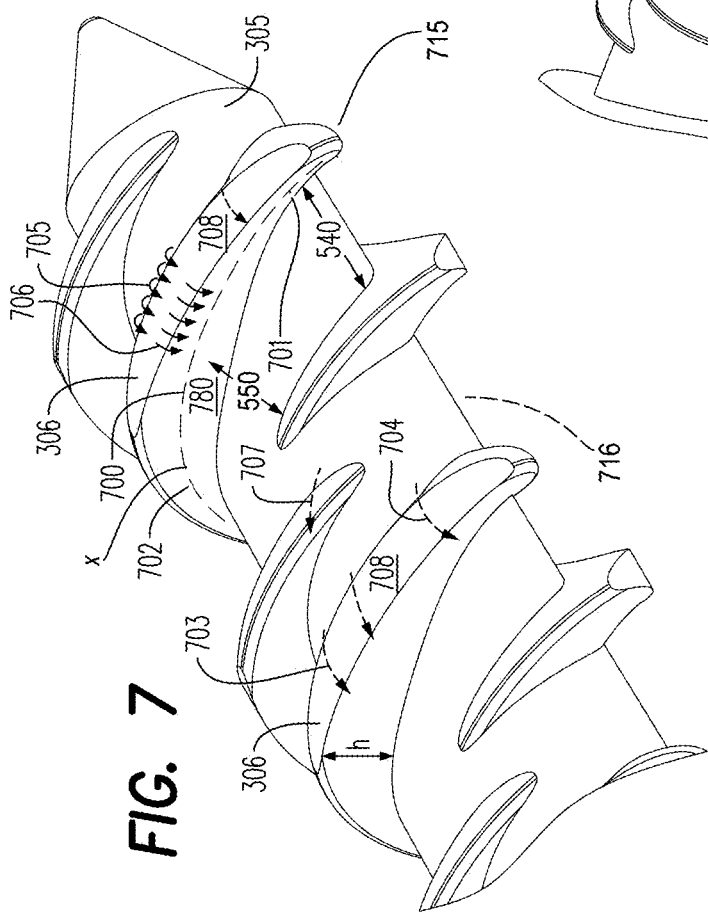
FIG. 7 shows an enlarged view of exemplary compound parabolic petals according to the disclosure.

Expansive gaps 550 are created in part by overcut parabolic portions 702 of the petals 306 as described with respect to FIG. 7. The expansive gaps 550 release a portion of the compression that the compressive gaps 540 create on the trabecular bone while maintaining some compression on the trabecular bone as the orthopedic fastener 300 is turned and advanced through the trabecular bone. Systematically releasing a portion of the compression reduces resistance against further compression of the trabecular bone and enhances uniformity of the compression along the length of the orthopedic fastener 300. For example, applying constant compression from an orthopedic fastener advancing through trabecular bone may compact the trabecular bone in one region such as the distal end of the orthopedic fastener. Compacting the trabecular bone in one region may increase the amount of force needed to further advance the orthopedic fastener, and thereby increase the risk of damage to the trabecular bone, and result in imbalanced compression at different points along the length of the orthopedic fastener.

Transition gaps 560 are areas between repeating sets 510 of petals 306 where compressed trabecular bone passes from one repeating set to a following repeating set. Transition gaps 560 maintain most of the compression created in the previous repeating set such that the trabecular bone may be further compressed in the successive repeating set. In the exemplary embodiment and sections thereof shown in FIGS. 3A-5, the length of successive repeating sets 510 decreases in a direction from the distal end 305 to the proximal end 304 as the distance between the petals 306 decreases as previously described. Accordingly, overall compression can be increased in each successive repeating set 510.

In the exemplary orthopedic fastener 300 and sections thereof shown in FIGS. 3A-5, each of the three petals 306 in each repeating set 510 has at least one compressive gap 540 and one expansive gap 550. Thus, with each full, 360 degree turn of the orthopedic fastener 300 during advancement, three cycles of compression and partial release is achieved for every repeating set 510 of petals 306 that is within the trabecular bone. Accordingly, in an exemplary method of orthopedic fastening trabecular bone is progressively compressed in this compress-partial release-compress fashion using an orthopedic fastener such as the exemplary orthopedic fastener 300 and features thereof shown in FIGS. 3A-5. The configuration of each petal 306 including the compressive gap 540 and expansive gap 550 is shown in further detail and described with respect to FIGS. 7 and 8.

With reference now to FIG. 7, a detailed view of an exemplary embodiment of petals, i.e., compound parabolic petals 306, is shown. Petals 306 project away from the shaft 303 in the height direction h and have a compound parabolic configuration. For purposes of the disclosure, a "compound parabolic petal" means a petal configured with a plurality of parabolic features including continuous parabolic structures and/or transitions such as those shown in FIG. 7 and described with respect thereto. The height h of compound parabolic petals 306 can be any suitable value depending on the particular application and requirements for an orthopedic fastener. Moreover, it could be modified to accommodate the variances in bone structure found in different medical conditions that are not optimal such as bone that has been compromised by Cancer or Tuberculosis as an example.

The compound parabolic structure of the petals 306 is also chosen to suit the particular application and requirements for an orthopedic fastener. With reference to the exemplary compound parabolic petal 306 shown in FIGS. 7 and 8, each petal 306 includes one proximal parabola 700 shifting from an undercut 701 to an overcut 702 parabolic aspect on a proximal side 780 (i.e., facing the proximal end 304 of shaft 303) and a lateral parabolic aspect 707 in a direction lateral to the minor diameter 395. The proximal parabola 700 creates the compressive gap 540 and expansive gap 550 respectively between the undercut 701 and overcut 702 parabolic aspects and an adjacent petal 306. Thus, as the orthopedic fastener 300 is turned and advanced through trabecular bone each compound parabolic petal 306 transitions from compressing the trabecular bone to releasing a portion of the compression creating the exemplary compress-partial release-compress progression.

The undercut 701 and overcut 702 parabolic aspects also have respective closed 704 and open 705 lateral parabolic aspects 707. The closed parabolic aspect 704 contributes to compression of trabecular bone by extending in towards the undercut parabolic aspect 701 to contain the trabecular bone in the undercut parabolic aspect 701. The open parabolic aspect 705 contributes to expansion of trabecular bone by extending away from the overcut parabolic aspect 702 to open additional space in the overcut parabolic aspect 702. Line x illustrates a contour of the proximal side 780 of the petal 306 representing geometrical radii along the length L of the shaft 300 from a leading edge 715 of the petal 306 to a trailing edge 716 (not visible on the other side of the shaft) of the petal 306. The contour x enhances axial compression of the trabecular bone along the shaft and thereby enhances radial compression of the trabecular bone 102 against the cortical wall 101.

Figure 8:
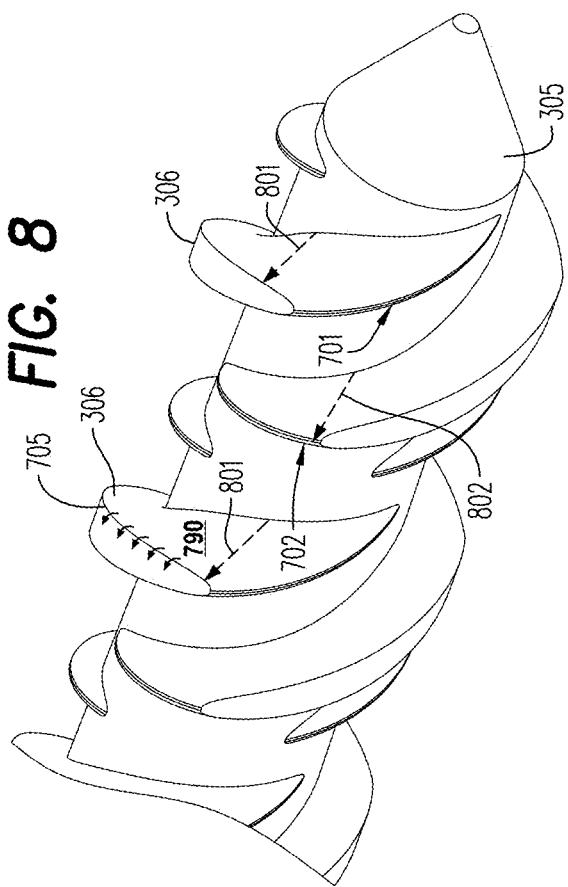
FIG. 8 shows an enlarged view of exemplary compound parabolic petals according to the disclosure.

With continuing reference to FIG. 7, each petal 306 has an arc (or, "capped") crest 708 extending between the proximal 780 and a distal 790 (i.e., facing the distal end 305 of shaft 303, as shown in FIG. 8) side of the petal 306. In the exemplary embodiment shown in FIG. 7, the arc crest 708 is parabolic along its length. Transition between the distal face 790 and the proximal face 780 of the petal 306 is via compound parabolic radii or aspects 705, 706 along each side of the arc crest 708 extending respectively into the overcut, open parabolic aspects 801, 802 (FIG. 8) of the distal side 790 and the undercut, closed parabolic aspect 701 and overcut, open parabolic aspect 702 of the proximal side 780. The compound parabolic radii or aspects 705, 706 allow for smooth transitions between the distal 790 and proximal 780 sides and reduces the occurrence of sharp edges.

With reference now to FIG. 8, the distal side 790 of the petal transitions from an open, overcut parabolic aspect 801 to a reduced overcut parabolic aspect 802. The open, overcut parabolic aspect 801 of the distal side 790 is configured adjacent to the open, overcut aspect 702 of the proximal side 780 of an adjacent petal 306. The reduced overcut parabolic aspect 802 is configured adjacent to the closed, undercut parabolic aspect 701 of the proximal side 780 of an adjacent petal 306. The gaps between respective portions of the proximal 780 and distal 790 sides of adjacent petals 306 form the compressive 540 and expansive 550 gaps.

With reference now to FIGS. 9A-10, an exemplary embodiment of an orthopedic fastener 900 having repeating sets 910 of two petals is shown. With reference to FIG. 9A, the exemplary orthopedic fastener 900 includes, among other things, a head portion 901, a tip 902, and a shaft 903 having a proximal end 904 connected to the head portion 901 and a distal end 905 connected to the tip 902 and extending therebetween. A connecting bulb 908 is connected to the head portion 901 and connects to additional components of an orthopedic fastening system such as the one shown in FIG. 11. A plurality of petals 906 including petals 906a, 906b, discussed further below, are arranged helically around the shaft 903 such that portions of different petals 906 circumferentially overlap along a length L of the shaft 903 and form gaps 1040, 1050, 1060 (explained in detail further below with respect to FIG. 10) between circumferentially overlapping portions of petals 906. The general configuration, variations, and operation of the two-petal fastener 900 follows the three-petal fastener 300 described above with respect to FIGS. 3A-3C, except that the two-petal fastener 900 has repeating sets 910 of two petals instead of three.

The exemplary helical configuration of the petals 906 and representative petals 906a and 906b are shown in the various perspective views of FIGS. 9A-9D. FIGS. 9A and 9B respectively show plan and top perspective views from the same side of the orthopedic fastener 900. FIG. 9C shows a top perspective view of the orthopedic fastener 900 from an opposite, or back side to that shown in FIGS. 9A and 9B. Petal 906a begins in the views of FIGS. 9A and 9B, wraps around the shaft as shown in FIG. 9C, and ends back in the view of FIG. 9A. Petal 906b begins in the view of FIG. 9C, wraps around the shaft as shown in FIGS. 9A and 9B, and ends in the views of both FIGS. 9B and 9C. FIGS. 9A-9C illustrate the overlapping configuration of the petals 906 in an exemplary embodiment. With continuing reference to the view shown in FIG. 9A and in a direction from the distal end 905 to the proximal end 904 of the shaft 903, petal 906a begins closest (as between petals 906a and 906b) to the distal end 905. On the other hand, in the view of FIG. 9C petal 906b begins closes to the distal end 905, overlaps petal 906a as shown in the views of FIGS. 9A and 9B, and ends farthest from the distal end 905 in the view of FIG. 9C. This overlapping helical configuration of the petals 906 contributes to the exemplary disclosed compression of trabecular bone. As shown in FIG. 9A, the arrangement of representative petals 906a and 906b constitutes a repeating set 910 of two petals that is repeated along the length L of the shaft 903 in the exemplary embodiment.

FIG. 9D shows the exemplary orthopedic fastener 900 shown in FIGS. 9A-9C from the perspective along the tip 902. The exemplary helical configuration of petals 906, by reference to representative petals 906a and 906b, is also achieved in part by spacing the beginning and ends of successive petals (e.g., 906a and 906b) at 180 degrees apart around the circumference of shaft 903.

Other dimensional aspects of the exemplary disclosed embodiment of an orthopedic fastener 900 shown in FIGS. 9A-9D are shown in FIG. 9E. As shown in FIG. 9E, and with continuing reference to FIG. 9A, the exemplary embodiment includes at least one distance, e.g., $D_1$, between successive petals 906 along the same circumferential angle on the shaft 903 and widths $W_1$-$W_2$ between petals 906. In one aspect of the exemplary embodiment shown in FIG. 9E, the distance between petals 906 progressively decreases in a direction from the distal end 905 to the proximal end 904. Accordingly, the distance between successive petals 906 along the same circumferential angle on the shaft 903 will progressively decrease from $D_1$, to $D_1$-$\Delta_1$, to $D_1$-$\Delta_1$-$\Delta_2$, and through to $D_1$-$\Delta_1$- ... $\Delta_n$, where $\Delta_1$, $\Delta_2$, ... and $\Delta_n$ can be any suitable value depending on the particular application and requirements for the orthopedic fastener 900. Similarly, the widths $W_1$ and $W_2$ between petals 906 will decrease respectively from $W_1$ and $W_2$ to $W_1$-$\delta_1$ and $W_2$-$\delta_2$, to $W_1$-$\delta_1$-$\delta_3$ and $W_2$-$\delta_2$-$\delta_4$, through to $W_1$-$\delta_1$-$\delta_x$ and $W_2$-$\delta_2$-$\delta_y$, where $\delta_1$, $\delta_2$, ... $\delta_y$ can be any suitable value depending on the particular application and requirements for the orthopedic fastener 900.

The exemplary two-petal fastener 900 may find application, by way of example, in cervical fixation procedures. Trabecular bone in the cervical spine is typically softer and spongier to support the head and neck and movement. Thus, distances between successive petals 906 along the same circumferential angle on the shaft 903 ($D_1$, etc.) may tend to be short as less distance is needed to achieve required compression. In the exemplary two-petal fastener 900, exemplary ranges of distances ($D_1$, etc.) between successive petals 906 along the same circumferential angle on the shaft 903 are from approximately 3 mm to about 1.5 mm. An exemplary width ($W_1$, etc.) between successive, adjacent petals 906 is approximately 1 mm and an exemplary range of heights h of petals is from approximately 0.15 mm to 1 mm. An exemplary range for the circumferential length of the petals 906 around the shaft 903 is from approximately 7 mm-10 mm and an exemplary range for the minor diameter of the shaft is approximately 2.5 mm-4.5 mm. An exemplary range for the shaft length L is approximately 6 mm-150 mm, and in the exemplary disclosed embodiment the shaft length is approximately 30 mm.

With reference now to FIG. 10, the configuration of petals 906 and gaps 1040, 1050, 1060 in the exemplary orthopedic fastener 900 shown in FIGS. 9A-9E is illustrated in additional detail. As shown in FIGS. 9A and 10, petals 906 in the exemplary embodiment are arranged in repeating sets 910 of two petals (e.g., 906a and 906b). Repeating sets 910 are representatively shown in the blown-up view of the distal end 905 in FIG. 10 and it is understood that such repeating sets continue up the shaft 903 to the proximal end 904 as in the exemplary embodiment shown in FIGS. 9A-10. The petals 906 are compound parabolic petals having a similar configuration as previously described with respect to FIG. 7.

The gaps 1040, 1050, 1060 between petals 906 include compressive gaps 1040, expansive gaps 1050, and transition gaps 1060. Similar to the exemplary three-petal orthopedic fastener 300 shown in FIGS. 3A-5, compressive gaps 1040 are created in part by undercut parabolic portions 701 (FIG. 7) of the petals 906. The undercut parabolic portions 701 "scoop" and compress trabecular bone in the compressive gaps 1040 as the orthopedic fastener 900 is turned and advanced through the trabecular bone in a manner as previously described with respect to the exemplary three-petal orthopedic fastener 300 and with reference to FIGS. 2 and 6. Expansive gaps 1050 are created in part by overcut parabolic portions 702 (FIG. 7) of the petals 906 in the manner described with respect to the exemplary three-petal orthopedic fastener 300. The expansive gaps 1050 release a portion of the compression that the compressive gaps 1040 create on the trabecular bone while maintaining some compression on the trabecular bone as the orthopedic fastener 900 is turned and advanced through the trabecular bone. Transition gaps 1060 are areas between repeating sets 910 of petals 906 where compressed trabecular bone passes from one repeating set to a following repeating set. Transition gaps 1060 maintain most of the compression created in the previous repeating set such that the trabecular bone may be further compressed in the successive repeating set. In the exemplary orthopedic fastener 900 and sections thereof shown in FIGS. 9A-10, the length of successive repeating sets 910 decreases in a direction from the distal end 905 to the proximal end 904 as the distance between the petals 906 decreases as previously described. Accordingly, overall compression can be increased in each successive repeating set 910.

In the exemplary orthopedic fastener 900 and sections thereof shown in FIGS. 9A-10, each of the petals 906 in each repeating set 910 has at least one compressive gap 1040 and one expansive gap 1050. Thus, with each full, 360 degree turn of the orthopedic fastener 900 during advancement, two cycles of compression and partial release is achieved for every repeating set 910 of petals that is within the trabecular bone. Accordingly, in an exemplary method of orthopedic fastening, trabecular bone is progressively compressed in this compress-partial release-compress fashion using an orthopedic fastener such as the exemplary orthopedic fastener 900 and features thereof shown in FIGS. 9A-10.

The exemplary two-petal orthopedic fastener 900 will generally not achieve the same amount of trabecular bone compression as the exemplary three-petal orthopedic fastener 300 because there is one less stage of compression in each repeating set 910 of petals 906. Further, the exemplary three-petal fastener 300 provides enhanced omnidirectional stability, where multi-directional forces may impact the attachment. On the other hand, the exemplary two-petal fastener 900 provides enhanced bi-directional stability for attachments in areas such as the length of the spine, where forces are concentrated in a finite number of directions such as up and down.

In other embodiments, an orthopedic fastener according to the disclosure may have repeating sets of any number of petals depending on, e.g., the desired application and manufacturing capabilities. Similarly, in general, an orthopedic fastener according to the disclosure may have any number of repeating sets, or none. For example, the petals may be arranged in an irregular or non-repeating order or according to any number of patterns without departing from the spirit and scope of this disclosure. Different applications may involve, for example, different trabecular bone structures including the density and liquid content of the trabecular bone in different bones/areas of the body, the load bearing of the bone, the patient, the nature of the injury, and other considerations discussed herein.

Figure 11:
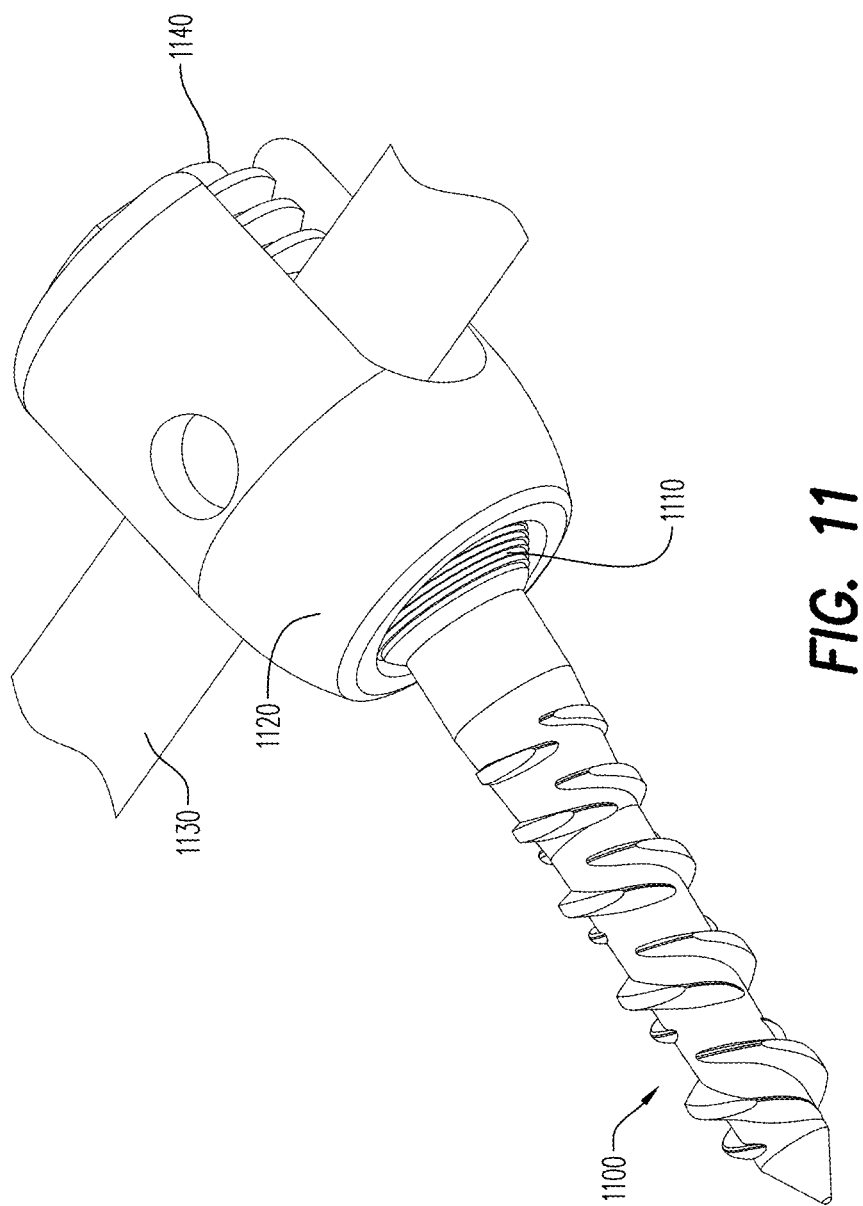

The exemplary and other embodiments of an orthopedic fastener according to the disclosure may generally be used with known surgical systems for attaching orthopedic fasteners. An exemplary surgical system is shown in FIG. 11. In the exemplary surgical system, an orthopedic fastener 1100 according to the disclosure is attached to a head body 1120 (also called a tulip) by polyaxial joint 1110. The polyaxial joint 1110 is created by, for example, inserting the connecting bulb 308, 908 of the exemplary three-petal 300 and two-petal 900 orthopedic fasteners into the head body 1120. The polyaxial joint 1110 allows the orthopedic fastener 1100 to pivot with respect to the head body 1120. In operation, a user (e.g., surgeon) will insert the orthopedic fastener 1100 into a bone by drilling a hole in one cervical wall of the bone, inserting the orthopedic fastener 1100 into the bone, and turning the orthopedic fastener 1100 using rod 1130 as a handle/torque generator to advance the orthopedic fastener 1100 through the trabecular bone. Set screw 1140 holds the rod 1130 in place within the head body 1120. Set screw 1140 may be any known screw or lock nut, or known device for locking components together. The polyaxial joint 1110 compensates for any differences between the angle at which the orthopedic fastener 1100 is inserted into the bone and the angle at which the rod 1130/head body 1120 are held during the insertion process by allowing the orthopedic fastener 1100 to pivot with respect to the head body 1120 and thereby maintain its trajectory into the bone as the head body 1120 is potentially moved by the surgeon.

The exemplary devices, systems, and methods disclosed herein are not limited to the specific embodiments described, but rather, features illustrated or described as part of one embodiment can be used on or in conjunction with other embodiments to yield yet a further embodiment. The disclosure is intended to include such modifications and variations. Further, steps described in, e.g., methods of manufacture and/or use may be conducted independently and separately from other steps described herein.

The present disclosure, in various embodiments, configurations and aspects, includes components, methods, processes, systems and/or apparatus substantially developed as depicted and described herein, including various embodiments, sub-combinations, and subsets thereof. The present disclosure, in various embodiments, configurations and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

Where necessary, exemplary ranges have been supplied, and those ranges are inclusive of all sub-ranges there between. Variations in the ranges for particular applications of the devices, systems, and methods according to the disclosed considerations may be varied according to a variety of factors including but not limited to the particular application for, e.g, different bones and/or locations such as spinal and/or other bone locations including but not limited to dental applications, facial or cosmetic applications, and or/other applications in which bone fastening and stabilization is necessary. The ranges may also depend on, for example, the age and condition of the patient, the forces that will act upon the fastener, the general level of activity of the patient, etc. The exemplary embodiments in this disclosure do not limit the use of the exemplary orthopedic fastener for any applications in which trauma to bone, or, in particular, trabecular bone is desired.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of."

The terms "determine", "calculate" and "compute," and variations thereof, as used herein, are used interchangeably and include any type of methodology, process, mathematical operation or technique.

The present disclosure has been presented for purposes of illustration and description and is not intended to limit the present disclosure to the form or forms disclosed herein. In the foregoing Detailed Description for example, various features of the present disclosure are grouped together in one or more embodiments, configurations, or aspects for the purpose of streamlining the disclosure. The features of the embodiments, configurations, or aspects of the present disclosure may be combined in alternate embodiments, configurations, or aspects other than those discussed above. This method of disclosure is not to be interpreted as reflecting an intention that the present disclosure requires more features than are expressly recited in each claim. Rather, as the following claims reflect, the claimed features may lie in less than all features of a single foregoing disclosed embodiment, configuration, or aspect. Thus, the following claims are hereby incorporated into this Detailed Description, with each claim standing on its own as a separate embodiment of the present disclosure.

Advances in science and technology may make substitutions possible that are not now contemplated by reason of the imprecision of language; these variations should be covered by the appended claims. Further, while this disclosure sets forth certain exemplary embodiments, various changes may be made and features may be substituted without departing from the contemplated scope. In addition, many modifications may be made to adapt a particular situation or material to this disclosure without departing from the essential scope thereof.

What is claimed is:

1. An orthopedic fastener, comprising:
   a head portion;
   a tip portion;
   a shaft having a proximal end connected to the head portion and a distal end connected to the tip portion; and
   a plurality of compound parabolic petals extending helically around the shaft and defining gaps between circumferentially overlapping portions of petals, wherein the petals are configured to compress trabecular bone in the gaps and in a direction perpendicular to the insertion direction of the orthopedic fastener in a bone.

2. The orthopedic fastener of claim 1, wherein the distance between petals decreases in a direction from the distal end to the proximal end.

3. The orthopedic fastener of claim 1, wherein the gaps include both compressive gaps and expansive gaps, and
   the compressive gaps are configured to compress trabecular bone and the expansive gaps are configured to release a portion of the compression created by the compressive gaps on the trabecular bone during insertion and advancement of the orthopedic fastener through a bone, thereby progressively compressing the trabecular bone in a compress-partial release-compress fashion.

4. The orthopedic fastener of claim 1, wherein the petals are arranged in repeating sets of petals along the shaft and the distance between corresponding petals in successive sets progressively decreases in a direction from the distal end to the proximal end.

5. The orthopedic fastener of claim 4, wherein each repeating set comprises two petals.

6. The orthopedic fastener of claim 5, wherein each repeating set comprises three petals.

7. The orthopedic fastener of claim 1, wherein each petal has a proximal face and a distal face, the proximal face has a transition between an undercut and an overcut parabolic portion, and the undercut parabolic portion is configured to compress trabecular bone.

8. The orthopedic fastener of claim 7, wherein the distal face has at least one overcut parabolic portion and the proximal face of a first petal is configured to compress trabecular bone between the proximal face of the first petal and the distal face of a second petal.

9. The orthopedic fastener of claim 1, wherein at least a portion of the shaft tapers in a direction from the proximal end to the distal end.

10. The orthopedic fastener of claim 1, wherein a height of the petals is between approximately 0.1 mm and 12.5 mm and a distance between petals is between approximately 1.5 mm and 15 mm.

11. The orthopedic fastener of claim 10, wherein the trabecular bone is cervical vertebral body trabecular bone.

12. The orthopedic fastener of claim 11, wherein the height of the petals is between approximately 0.15 mm and 1 mm, and the distance between petals is between approximately 1.5 mm and 3 mm.

13. The orthopedic fastener of claim 10, wherein the trabecular bone is lumbar trabecular bone.

14. The orthopedic fastener of claim 13, wherein the height of the petals is between approximately 0.2 mm and 1.0 mm, and the distance between petals is between approximately 2.5 mm and 4 mm.

15. The orthopedic fastener of claim 1, wherein the petals have compound curved leading and trailing edges configured to compress trabecular bone and prevent lacerations.

16. The orthopedic fastener of claim 1, wherein the tip portion is formed in a shape and from a material capable of penetrating trabecular bone.

17. The orthopedic fastener of claim 16, wherein the tip portion is cone-shaped.

18. The orthopedic fastener of claim 16, wherein the material includes at least one of cobalt, chrome, and titanium.

19. An orthopedic fastening system, comprising:
an orthopedic fastener having:
a head portion;
a connecting bulb connected to the head portion;
a tip portion;
a shaft having a proximal end connected to the head portion and a distal end connected to the tip portion; and
a plurality of compound parabolic petals extending helically around the shaft and defining gaps between circumferentially overlapping portions of petals, wherein the petals are configured to compress trabecular bone in the gaps and in a direction perpendicular to the insertion direction of the orthopedic fastener in a bone;
an annular, polyaxial articulating head having first and second apertures along a diameter of the polyaxial articulating head; and,
a torsion rod, wherein
the polyaxial articulating head is configured to receive the connecting bulb, move polaxially about the connecting bulb, and receive the torsion rod through the first and second apertures, and,
the polyaxial articulating head is further configured to rotate and thereby advance the orthopedic fastener through a bone when the torsion rod is turned and maintain the path of the orthopedic fastener through the bone regardless of the polyaxial orientation of the articulating head.

20. A compound parabolic petal for an orthopedic fastener, comprising:
a proximal face;
a distal face; and,
a capped crest,
wherein the proximal face has a transition between an undercut and an overcut parabolic portion and the undercut parabolic portion is configured to compress trabecular bone,
the distal face has at least one overcut parabolic portion, and
the capped crest has compound curved leading and trailing edges.

* * * * *